United States Patent [19]

Riley et al.

[11] Patent Number: 4,571,391

[45] Date of Patent: Feb. 18, 1986

[54] CHROMIUM ACETYLACETONATE AS A DIETARY SUPPLEMENT AND PHARMACEUTICAL AGENT

[75] Inventors: Dennis P. Riley; Mark M. Anderson, both of Cincinnati; John T. Rotruck, Oxford, all of Ohio

[73] Assignee: The Procter & Gamble Company, Cincinnati, Ohio

[21] Appl. No.: 205,042

[22] Filed: Nov. 7, 1980

Related U.S. Application Data

[63] Continuation-in-part of Ser. No. 21,382, Mar. 19, 1979, abandoned.

[51] Int. Cl.$^4$ .............................................. A61K 37/26
[52] U.S. Cl. ......................................... 514/4; 514/505
[58] Field of Search ............................... 424/178, 287

[56] References Cited

U.S. PATENT DOCUMENTS 3,914,410 10/1975 Godfrey .............................. 424/131
3,925,433 12/1975 Abdel-Monem ............. 260/438.5 R

OTHER PUBLICATIONS

Schwartz et al—"Archives of Biochemistry and Biophysics", vol. 85, pp. 292–295 (1959).
Mertz—"Nutrition Reviews, vol. 33, No. 5, May 1975, pp. 129–135.
The Merck Index, Ninth Edition, 1976, pp. 659 and 1223, Merck & Co., Inc., Rahway, N.J., U.S.A.
Jeejeebhoy et al., "Chromium Deficiency, Glucose Intolerance, and Neuropathy Reversed by Chromium Supplementation, in a Patient Receiving Long-Term Total Parenteral Nutrition", Am. J. Clin. Nut., vol. 30 (1977) pp. 531–538.
Freund et al., "Chromium Deficiency During Total Parenteral Nutrition", J. Am. Med. Assoc., vol. 241, No. 5 (1979) pp. 496–498.

Primary Examiner—Frederick E. Waddell
Attorney, Agent, or Firm—Eric W. Guttag; Steven J. Goldstein; Richard C. Witte

[57] ABSTRACT

Chromium(III) tris-acetylacetonate, a coordinatively saturated, stable chromium(III) compound provides a dietary chromium supplement for humans and lower animals and is a useful hypoglycemic pharmaceutical agent for treating diabetes, especially when used in conjunction with insulin therapy.

3 Claims, No Drawings

CHROMIUM ACETYLACETONATE AS A DIETARY SUPPLEMENT AND PHARMACEUTICAL AGENT

This is a continuation-in-part of U.S. patent application Ser. No. 021,382, filed March 19, 1979, now abandoned.

TECHNICAL FIELD

The instant invention relates to chromium (III) tris-acetylacetonate and its use as a dietary supplement and hypoglycemic pharmaceutical agent in humans and lower animals.

Chromium has been determined to be an essential micronutrient for the maintenance of normal glucose tolerance in animals. The chromium cation exists in oxidation states of plus II, plus III and plus VI. Chromium (II) is very readily oxidized to chromium (III) on exposure to atmospheric oxygen. Chromium (VI) is toxic to man and animals. The chromium tris-acetylacetonate used in this invention is a complex chromium compound in the (III) oxidation state.

Chromium (III) is safe and required in a proper dietary regimen of animals and humans. Thus, as used herein, "chromium" is intended to mean the chromium cation in the III oxidation state. The action of chromium is closely associated with that of insulin. Chromium deficiency in humans has been reported as the cause of a reduced response of insulin-sensitive tissue to the hormone, manifested by impaired glucose metabolism.

The use of various chromium (III) salts for supplementing diets of mammals has been reported in the scientific literature. Persons particularly in need of chromium(III) supplementation include diabetics (*diabetes mellitus*) and those suffering from a dietary chromium deficiency.

Chromium deficiency may result in impaired glucose metabolism in one or more of the following situations: (1) dietary chromium deficiency, (2) juvenile-onset diabetes, and (3) maturity-onset diabetes.

In the case of dietary chromium deficiency, if a mammal obtains less chromium from its diet than is used or excreted from the body on a daily basis, the resulting negative chromium balance will eventually deplete body stores of chromium to the point where many bodily functions, especially insulin-sensitive processes, are impaired. Dietary supplementation with a form of chromium that is absorbable from the gastrointestinal tract and able to undergo biological interaction with insulin-sensitive systems would alleviate this situation.

In juvenile-onset diabetes, there is essentially a complete cessation of insulin production by the pancreas. Lack of circulating insulin results in severe hyperglycemia. Insulin therapy is required to maintain normal blood glucose levels, but treatment is difficult and often results in wide variations in blood glucose values. In addition, it is known that elevated blood glucose results in mobilization of body stores of chromium which is then nearly quantitatively excreted in the urine. Thus, it is apparent that a victim of juvenile-onset diabetes would mobilize and excrete more chromium than a normal individual. If this chromium is not replaced via the diet or by therapeutic supplementation, the resulting chromium deficiency may induce a refractory response to exogenous insulin, exacerbating the diabetic symptoms and requiring ever increasing doses of insulin to maintain normal blood glucose levels. A biologically-active form of chromium, given either as a dietary supplement or as an adjunct to, or in combination with, insulin therapy, would help to prevent the development of this situation and, in some instances, allow the amount of insulin administered to maintain normal blood glucose levels to be substantially decreased.

Maturity-onset diabetes presents a different set of conditions, but with an end result similar to that of juvenile-onset diabetes. In maturity-onset diabetes, the pancreas continues to secrete insulin, often at higher than normal levels. However, due to impaired tissue sensitivity or defective insulin, this endogenous insulin elicits little or no physiological response. Normal blood glucose levels are approximated either by injection of exogenous insulin or by oral administration of hypoglycemic drugs which stimulate the pancreas to produce even more insulin. As in juvenile-onset diabetes, the abnormally high blood glucose levels would be expected to lead to increased chromium mobilization and excretion, resulting in eventual chromium deficiency and aggravation of the diabetic situation. Since chromium is necessary for optimum in vivo action of insulin, the importance of improving the effectiveness of insulin in a maturity-onset diabetic by administering an absorbable and effiicacious form of chromium is clear. In those diabetic individuals who are chromium deficient, this would allow lowering the total dosage of insulin or oral hypoglycemic drug, even to the point that administration of insulin or oral hypoglycemic drugs could be halted without affecting the patient.

One paradox of chromium deficiency is that while many foods naturally contain entirely adequate levels of chromium, the chromium is lost during processing. With the advent and prevalence of processed foods, it has become increasingly necessary to supplement the diet with chromium. This task has proved to be difficult because the chemical form in which chromium(III) is presented to the body is highly determinative of its extent of absorption from the gastrointestinal tract, and thus its bioactivity, at effective, yet safe dosage levels.

The chromium(III) tris-acetylacetonate of the instant invention has, despite its stability, been found to be absorbed from the gastrointestinal tract of mammals in significant quantity. More importantly, it has been found to have substantial biological activity.

In accordance with this invention, chromium(III) tris-acetylacetonate in safe and effective amounts can be used to treat impaired glucose metabolism due to diabetes mellitus, as well as to treat more generalized problems associated with chromium deficiency.

BACKGROUND ART

Many of the chemically familiar chromium compounds have been found to be ineffective for delivering chromium(III) ions orally to the body. Accordingly, efforts to treat mammals in need of the chromium(III) ion have involved the use of organic complexes of chromium which are somewhat ill-defined and rather unstable.

U.S. Pat. No. 3,914,410, Godfrey (1975) discloses addition of trace amounts of certain chromium salts to sugar to produce a fortified composition which is said to reduce the severity or incidence of atherosclerosis or adult-onset diabetes. Unrefined sugar contains appreciable quantities of chromium, but as the sugar is refined the chromium is removed.

U.S. Pat. No. 3,925,433, Abdel-Monem, et al. (1975) describes complexes formed between chromium and α-amino acids. The chromium in these complexes is said to be readily absorbed, distributed and utilized within the biochemical system of animals and humans. The rate of absorption and distribution is said to be substantially higher than that of chromium chloride.

Shwartz and Mertz, *Archives of Biochemistry and Biophysics*, Vol. 85, p. 293 (1959) state that very stable chromium complexes, for example the bidentate chromium acetylacetonate and several ethylenediamine complexes, seem to be metabolically inert.

Mertz, *Nutrition Reviews* 33, No. 5, p. 130 (May 1975) states that "simple" chromium compounds, for example the chloro, aquo, or acetate coordinate chromium compounds or complexes, do not meet the criteria of absorption and bioavailability needed for use as cofactors for insulin.

DISCLOSURE OF INVENTION

Unexpectedly and contrary to the view expressed in the scientific literature, chromium(III) tris-acetylacetonate has now been discovered to be a suitable form in which chromium can be delivered to the body with good gastrointestinal absorption and bioactivity.

Chromium(III) tris-acetylacetonate is more stable than chromium complexes heretofore known for use in the diet. Chromium(III) tris-acetylacetonate is rather water insoluble, heat stable, and very stable to acid. Being coordinatively saturated, the chromium ion of this compound does not olate, i.e., hydrolyze with attendant polymerization resulting in the formation of insoluble chromium species at the higher pH's of the intestine. Despite the described degree of stability, the chromium(III) tris-acetylacetonate is unexpectedly absorbable in the gastrointestinal tract. Unlike many other inorganic chromium compounds, the chromium(III) tris-acetylacetonate displays excellent biological activity in humans and lower animals, and acts as a cofactor with insulin to improve insulin-sensitive glucose metabolism.

Chromium(III) tris-acetylacetonate (abbreviated hereinafter as "Cr (acac)$_3$") is represented by the general formula

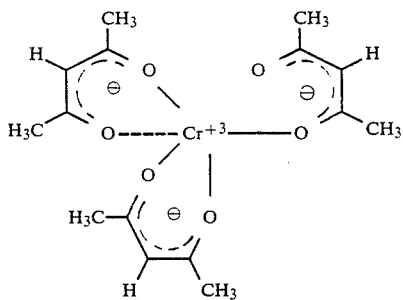

The present invention, accordingly, encompasses the use of Cr (acac)$_3$ as a dietary supplement.

This invention also provides a convenient method for supplementing foods from which the naturally occurring chromium has been removed by means of the bioavailable, bioactive Cr (acac)$_3$.

This invention also encompasses a method for treating non-insulin dependent diabetics comprising administering safe and effective amounts of Cr (acac)$_3$.

Chromium is known to be a co-factor for insulin. Accordingly, this invention also provides a method for treating insulin-dependent diabetic patients by concurrently administering safe and effective amounts of CR (acac)$_3$ and insulin to the diabetic.

It is noteworthy that the heat stability of the CR (acac)$_3$ allows it to be incorporated in food products prepared at high temperatures without loss of nutritional value. Examples of such food products include those obtained from soybean protein.

In accordance with the foregoing, the instant invention encompasses Cr (acac)$_3$ in unit dosage forms, in combination with insulin, in combination with oral hypoglycemic agents, and in foods and dietary supplements, e.g., vitamin/mineral preparations.

BEST MODE

Within the realm of sound medical judgment, the dosage of Cr (acac)$_3$ will vary with the particular condition being treated, the severity of the condition, and the duration of treatment employed. However, single dosages can range from 1 to 700 micrograms (μg) per kg of body weight, preferably 7 to 70 μg per kg. (Unless otherwise specified, the unit designated "μg per kg" as used herein refers to μg per kg of body weight.) The higher dosages within this range are usually employed for therapeutic use in cases of severe chromium deficiency and in diabetes therapy, whereas the lower dosages are appropriate for maintaining adequate dietary chromium levels. For therapeutic use, up to 4 dosages per day can be used routinely, but this can be varied with the needs of the patient, consistent with a sound benefit:risk ratio.

Preferably, dosages ranging from about 7 μg to about 70 μg per kg are employed when the Cr (acac)$_3$ is administered orally.

For parenteral administration (subcutaneous, intraperitoneal, intramuscular) dosages are preferably from about 3 to about 500 μg per kg per day. For long-term parenteral infusion (intravenous) the most highly preferred dosage range is from about 1 to about 100 μg per kg per day.

The Cr (acac)$_3$ is sparingly soluble in water. Parenteral administration can be carried out in ethanol/water mixtures.

For purposes of oral administration, the Cr (acac)$_3$ can conveniently be formulated as capsules, tablets or granules. Convenient unit dosage forms of Cr (acac)$_3$ comprise from about 10 μg to about 0.5 grams of Cr (acac)$_3$ and a pharmaceutical carrier. For treatment of non-human animals, the Cr (acac)$_3$ is preferably incorporated in animal feed, feed supplements or feed concentrates.

The preferred concentration range of the Cr (acac)$_3$ as described hereinabove in unit dosage forms intended for use by humans and small domesticated animals is from about 1.0 μg to about 2000 μg, more preferably from 350 μg to 1750 μg. A higher concentration range from about 2 mg to about 500 mg is the preferred unit dosage form intended for treatment of larger, non-ruminant animals, e.g., horses and the like.

Convenient compositions for oral administration of Cr (acac)$_3$ can also take the form of troches, chewable tablets and foodstuffs.

The term "pharmaceutical carrier" as used herein denotes any of the usual pharmaceutical excipients, including solid or liquid fillers, diluents, tableting aids, encapsulating substances, and the like. Some examples of the substances which can serve as pharmaceutical carriers for Cr (acac)$_3$ include sugars, such as lactose, glucose and sucrose; starches, such as cornstarch and potato starch; cellulose and its derivatives, such as sodium carboxymethylcellulose, ethylcellulose, cellulose acetate and powdered tragacanth; malt; gelatin; talc; stearic acids; magnesium stearate; calcium sulfate; vegetable oils, such as peanut oil, cottonseed oil, sesame oil, olive oil, corn oil and oil of theobroma; polyols, such as propylene glycol, glycerine, sorbitol, mannitol, polyethyleneglycol; agar; alginic acid; saline; and phosphate buffer solutions, as well as other non-toxic, compatible substances typically used in pharmaceutical formulations. Wetting agents and lubricants, such as sodium lauryl sulfate, as well as coloring agents, flavoring agents and preservatives can also be present. Tableting is done using conventional techniques. Gelatin capsules are another mode of administration.

The pharmaceutical carrier employed in conjunction with the Cr (acac)$_3$ is used at a concentration sufficient to provide a practical size to dosage relationship. Preferably, the pharmaceutical carrier comprises from about 0.1% to about 99% by weight of total composition.

The Cr (acac)$_3$ can be conveniently included in standard vitamin, mineral or mixed vitamin/mineral compositions to provide an excellent dietary supplement. The chemical and heat stability of Cr (acac)$_3$ assures that it will not undesirably interact with various foodstuffs, vitamins, minerals, and pharmaceutical excipients.

It will be appreciated that the present invention is useful not only in humans but also in lower animals in treating similar disease states involving the impairment of glucose metabolism and for general overall health and well-being.

Animal feed compositions to which the Cr (acac)$_3$ of this invention can be added generally include as feedstuffs a cellulosic roughage component such as hay, straw, plant hulls, corn cobs, and the like. Protein-containing components such as whole grains, including corn, wheat, barley, oats, rye, millet and alfalfa are typically included.

The following tests illustrate the bioavailability of Cr (acac)$_3$ and its interaction with insulin to lower blood glucose levels.

Animal Testing

Criteria for a nutritional or pharmaceutical chromium supplement include: it must be readily absorbed into the body from the gastrointestinal tract, and it must be able to exert a biological effect on insulin-sensitive processes in vivo. The animal experiments described below demonstrate that Cr (acac)$_3$ meets both of these requirements.

Absorption: Experiments were performed in order to measure the intestinal absorption of chromium from Cr (acac)$_3$. Cr (acac)$_3$ radiolabeled with $^{51}$Cr was prepared, delivered by stomach tube to the gastrointestinal tracts of adult rats and the distribution of radioactivity in the animals' tissues and excretia measured as a function of time. For the purposes of these experiments, $^{51}$Cr radioactivity found in the urine, bile and carcass tissues, minus that found in the gastrointestinal tract, represents absorbed chromium. Radioactivity in the feces and gastrointestinal tract represents non-absorbed chromium. The results of these experiments show that the majority of the chromium from orally dosed Cr (acac)$_3$ is absorbed from the gastrointestinal tracts of the rats, while less than 4% of the radioactivity from $^{51}$CrCl$_3$.6H$_2$O dosed under similar conditions is absorbed.

Materials and Methods: $^{51}$CrCl$_3$.6H$_2$O, 180 $\mu$Ci/$\mu$g, was obtained from Amersham-Searle Corp. $^{51}$Cr(III)-tris-acetylacetonate was prepared as follows: One mCi of $^{51}$CrCl$_3$.6H$_2$O was washed into a flask with 30 ml absolute ethanol, then dried under vacuum with gentle heating (60°–70° C.). Twenty mg unlabeled CrCl$_3$.6H$_2$O in 5 ml ethanol was added to the flask along with $2.25 \times 10^{-4}$ moles of acetylacetone. The contents of the flask were mixed thoroughly and $2.25 \times 10^{-4}$ moles of KOH in H$_2$O was added dropwise with constant mixing. The solution was refluxed with gentle heat and constant stirring for 2 hours. The solvent was removed under vacuum and the solid was dissolved in chloroform. The faintly red-blue solution was chromatographed through a $3 \times \frac{1}{2}''$ activated alumina column. The purple band was eluted and evaporated to dryness under vacuum. The resultant solid was dissolved in ethanol and its visible electronic spectrum recorded. Absorbance maxima at $\lambda=560$ nm, 410 nm and 388 nm, which correspond with literature values for authentic Cr(III)tris-acetylacetonate in ethanol, were found. Concentration was calculated based on a molar extinction coefficient for the complex at $\lambda=560$ nm of 66. Radioactivity was measured and the final specific activity of the preparation was calculated.

The animals used in these experiments were male CD Sprague-Dawley descended rats (The Charles River Breeding Laboratories, Inc.), given free access to Purina Laboratory Chow and tap water and housed in individual stainless steel cages. Rats weighed approximately 200 grams at the time of the experiments and were kept without rations for 18 hours prior to dosing. Bile duct cannulations were performed on the animals (under pentobarbital anesthesia) immediately prior to dosing. Each rat was dosed by stomach tube with either 1.0 ml of slurried Purina Laboratory Chow containing 2 to 5 $\mu$Ci $^{51}$Cr as Cr (acac)$_3$ or 0.75 ml H$_2$O containing 2 to 5 $\mu$Ci $^{51}$Cr as CrCl$_3$. 6H$_2$O. Whole-body radioactivity was determined in each animal immediately after dosing. Rats were fitted with plastic tail cups to facilitate collection of feces and placed in stainless steel mesh restraining cages with free access to food and water. All feces, urine and bile were collected. After 24 hours, animals were sacrificed and $^{51}$Cr-radioactivity in selected organs, carcass, gastrointestinal tract, urine, feces and bile determined. Radioactivity was measured in a whole body gamma counter with a 6-inch NaI(Tl) detector.

Results: Over 60% of the radioactivity from the orally dosed $^{51}$Cr (acac)$_3$ was absorbed from the gastrointestinal tracts of the test animals, while less than 4% of the label from $^{51}$CrCl$_3$.6H$_2$O dosed under similar conditions was absorbed, as shown in Table I. Radioactivity from $^{51}$Cr (acac)$_3$ appeared in the bile within 2 hours after dosing, indicating that chromium is very rapidly absorbed from a diet slurry. In contrast, no radioactivity from $^{51}$CrCl$_3$.6H$_2$O appeared in the bile at any time after dosing. Only 24% of the $^{51}$Cr (acac)$_3$ radioactivity was accounted for by the gastrointestinal tracts and feces. These sites contained nearly 95% of the radioactivity from $^{51}$CrCl$_3$.6H$_2$O. Urine radioactivity accounted for 29 and 1% of dosed label for the $^{51}$Cr (acac)$_3$ and $^{51}$CrCl$_3$.6H$_2$O dosed animals, respectively. Four percent of dosed radioactivity from $^{51}$Cr (acac)$_3$ and 1% from $^{51}$CrCl$_3$.6H$_2$O was retained in the carcasses. One hundred percent material balances were not obtained due to losses on cage and collection device surfaces, and to effects of differences in sample geometry on counting efficiency.

TABLE I

| $^{51}$Cr(III) Distribution - Orally Dosed With Either $^{51}$Cr(III) Tris-Acetylacetonate or $^{51}$CrCl$_3$.6H$_2$O | | | | | |
|---|---|---|---|---|---|
| | % of Dosed Radioactivity | | | | |
| Dosed Material* | Bile | Urine | Feces | GI Tract | Carcass |
| $^{51}$Cr(III) tris-acetylacetonate | 30 | 29 | 8 | 16 | 4 |
| $^{51}$CrCl$_3$.6H$_2$O | 0 | 1 | 95 | 2 | 1 |

*Four animals per group

Discussion: The results clearly show that the chromium from Cr (acac)$_3$ is much more absorbable from the gastrointestinal tracts of rats than is the chromium from CrCl$_3$.6H$_2$O. Thus, Cr (acac)$_3$ is stable enough to prevent ligand dissociation in the acidic environment of the stomach, allowing the complex to enter the intestines intact. The acetylacetonate ligands prevent chromium olation in the neutral-to-slightly alkaline small intestine, allowing efficient absorption of the metal. From this experiment, it is not clear whether the intact Cr (acac)$_3$ complex is absorbed or whether the ligand is broken down at the intestinal surface and the free metal absorbed. These results represent a very remarkable quantitative in vivo absorption of a structurally defined form of chromium(III) reported to date.

Biological Activity: Tuman (Tuman, Biological Effect of Glucose Tolerance Factor (GTF) and Inorganic Chromium(III) on Normal and Genetically Diabetic Mice, Ph.D. Thesis, State University of New York, Upstate Medical Center, 1975) has shown that a genetically diabetic strain of mice respond to chromium preparations shown to have in vitro biological activity with lowered non-fasting blood glucose (NFBG) levels. We have used this animal model, which mimics human maturity-onset diabetes, to show that Cr (acac)$_3$ is biologically active and acts with insulin in lowering the NFBG levels of these mice.

Materials and Methods: Male genetically diabetic mice, strain C57 BL/KsJ (db/db) were obtained from Jackson Laboratories. They were housed in individual stainless steel cages with free access to Purina Laboratory Chow Pellets and tap water. Mice were used for experiments when they were 7 to 9 weeks old (average body weight of approximately 34 g).

The first group of mice received a sham (control) dose of 26% ethanol/water (v/v), injected intraperitoneally (100 μl/animal). The second group of mice received a subcutaneous injection of insulin (Regular Iletin, Eli Lilly and Company), 1.0 unit in 100 μl normal saline per mouse. The third group of mice received an intraperitoneal injection containing 35 μg Cr (acac)$_3$ (equivalent to 5 μg chromium) in 100 μl 26% ethanol/water (v/v) per mouse. The fourth group of mice received both a subcutaneous injection of 1.0 unit of insulin in 100 μl normal saline per mouse and an intraperitoneal injection of 35 μg Cr (acac)$_3$ in 100 μl 26% ethanol water (v/v). Exactly 60 minutes after dosing, blood samples were obtained from the mice via retro-orbital sinus punctures into heparinized hematocrit tubes. Blood samples were centrifuged to obtain plasma. Plasma glucose concentrations were determined on a Beckman Glucose Analyzer, according to the manufacturer's instructions. All dosing solutions were prepared fresh the morning of the experiment.

Results: Results of this experiment are summarized in Table II. The extent of the diabetes-induced hyperglycemia is indicated by the NFBG level of the sham-dosed (control) mice of 590 mg/dl. The corresponding value for non-diabetic age matched mice is approximately 110 mg/dl. The 23% decrease in NFBG level induced by 1 unit of insulin/mouse was significantly different from the control value. Cr (acac)$_3$ alone was essentially without effect, illustrating the functional inactivity of the circulating insulin in the test animals. However, the combination treatment of insulin and Cr (acac)$_3$ gave nearly a 50% decrease in NFBG levels, a value which was significantly different from the results of all the other treatments. The more than additive effect of the two treatments in combination indicates that the activity of functional insulin is enhanced, i.e., it exerts its optimum biological activity, in the presence of ample levels of Cr (III), as provided by the Cr (acac)$_3$.

TABLE II

| The Effect of Insulin and Cr(III) Tris-Acetylacetonate on Non-Fasting Blood Glucose Levels in Genetically Diabetic Mice | | | |
|---|---|---|---|
| Treatment Group | Number of Mice | Mean Plasma* Glucose Conc. at 60 Minutes mg/dl 1 Std. Dev. | % Decrease from Control |
| Sham (control) | 7 | 590 ± 62 A | — |
| Insulin | 7 | 454 ± 90 B | 23 |
| Cr(III) Tris-acetylacetonate | 7 | 559 ± 118 A,B | 5 |
| Insulin + Cr(III) Tris-acetylacetonate | 7 | 299 ± 112 C | 49 |

*Differences between mean values followed by different letters are significant (P < 0.05) by Student's T Test.

Industrial Applicability

Since the compound Cr (acac)$_3$ is known in the art, the preparation thereof does not constitute part of this invention. The compound can conveniently be prepared in the following manner.

The art-disclosed preparation of Cr (acac)$_3$ involves the treatment of freshly precipitated hydrous chromium(III) oxide with acetylacetone. The preferred preparation disclosed here involves exact pH control through the homogeneous generation of ammonia (by the hydrolysis of urea) in a solution of a chromium(III) salt and acetylacetone. The operations involved are simple and convenient to perform.

To 100 ml. of water are added 2.66 g of chromium(III) chloride 6-hydrate (0.01 mol) and, after complete solution, 20 g of urea and 6 g of acetylacetone (0.06 mol). The reaction mixture is covered with a watch glass and heated overnight on a steam bath. As the urea hydrolyzes to release ammonia, deep maroon plate-like crystals of Cr (acac)$_3$ form. These are removed by suction filtration and dried in air.

The crude air-dried compound is dissolved in 20 ml of hot benzene, and 75 ml of hot petroleum ether is added slowly. The mixture is cooled to room temperature, chilled in a mixture of ice and salt, and filtered. The crystals are air-dried. The yield is at least 2.9 g (83%); the melting point is 216° C. Anal. Calcd. for Cr(C$_5$H$_7$O$_2$)$_3$: Cr, 14.90; C, 51.57; H, 6.06. Found: Cr, 15.06; C, 51.70; H, 6.08. (*Inorganic Synthesis* Vol. 5, p.

130; *Handbook of Preparative Inorganic Chemistry*, Vol. II, p. 1383 (edited by G. Brauer).

Cr (acac)$_3$ is a deep red-violet crystalline material with a melting point of 216° C. and a boiling point of 340° C. It is a neutral complex that is soluble in alcohols, chloroform, acetone and other common organic solvents, but is rather insoluble in water. Molecular weight determinations in organic solvents show that Cr (acac)$_3$ is a mononuclear and undissociated complex in such solvents. This complex is stable even in moderately acidic conditions in water. For example, it can be prepared in acidic water.

The Cr (acac)$_3$ exists as two enantiomeric (mirror-image) isomers, the Δ and Λ forms. They are chemically indistinguishable, but can be isolated as discrete, optically-active materials. The electronic spectrum of the complex in the visible region is characterized by two bands whose absorption maxima in ethanol are at 410 nm. and 560 nm. Their molar absorptivities are 158 and 66, respectively. These spectral features aid in detecting the presence and concentration of Cr (acac)$_3$ in solution.

As used herein, Cr (acac)$_3$ represents both enantiomeric isomers and mixtures thereof.

The chemical and heat stability of Cr (acac)$_3$ allows it to be formulated in all manner of compositions without loss of its nutritional value.

Thus, Cr (acac)$_3$ can be used as a diet supplement in food, in unit dosage forms, as an additive to other diet supplements such as vitamins and minerals, and in combination with insulin solutions and various hypoglycemic agents.

The known forms of insulin: regular, prompt, insulin zinc and crystalline-zinc, Semilente ®, isophane insulin suspension (NPH insulin) and insulin zinc suspension, Lente ®, globin zinc insulin, protamine zinc insulin suspension, extended insulin zinc suspension Ultralente ®, are all useful in pharmaceutical mixtures with Cr (acac)$_3$ for intramuscular injection.

The oral hypoglycemic agents useful with Cr (acac)$_3$ in the manner of this invention are of the known commercial types. They include the sulfonylurea compounds tolbutamide, chlorpropamide, acetohexamide and tolazamide; and the bisguanide compound phenformin.

Dosage of insulin will, of course, be determined by the attending physician, according to the needs of the patient. In the present invention, from about 5 units to about 70 units of insulin will be administered per day concurrently with the Cr (acac)$_3$ Likewise, the oral dosage of non-insulin hypoglycemic agents can be adjusted to the needs of the individual patient, but generally ranges from about 0.5 g. to about 5 g., on a daily basis, depending, of course, on the type of hypoglycemic agent.

The following examples illustrate the practice of this invention. The scope of the invention is, however, not limited by the scope of the examples.

EXAMPLE I

Gelatin capsules are prepared by conventional methods, comprising:

| Ingredient | μg per capsule |
|---|---|
| Cr (acac)$_3$ | 500 |
| Starch | 55600 |

The above capsule administered orally once daily substantially helps decrease glucose level in the blood of a patient weighing approximately 70 kilograms afflicted with the diabetic conditions described herein.

EXAMPLE II

Tablets are prepared by conventional methods, as follows:

| Ingredient | μg per capsule |
|---|---|
| Cr (acac)$_3$ | 1500 |
| Lactose | 40000 |
| Starch | 2500 |
| Magnesium stearate | 1000 |

When administered orally once daily the above tablet substantially decreases the glucose level in the blood of a diabetic patient weighing approximately 70 kilograms. Ingested one per day, the tablets of Example II are also useful as dietary supplements to maintain adequate Cr(III) levels in the diet of humans and lower animals.

EXAMPLE III

Meat analog compositions containing Cr(acac)$_3$ are prepared in the conventional manner, as follows:

| Ingredient | Parts by Weight |
|---|---|
| Extruded soy protein granules | 29.47 |
| Soy protein binder (egg white) | 5.20 |
| Solid Crisco ® shortening | 15.03 |
| Cr (acac)$_3$ | 0.001 |
| Coloring | 0.04 |
| Water and flavor to | 100 |

EXAMPLE IV

A multivitamin/mineral composition for human and Veterinary use is formulated with Cr (acac)$_3$ as follows:

| Ingredient | Amount |
|---|---|
| Vitamin A | 5,000 USP Units |
| Vitamin D | 400 USP Units |
| Thiamine (Vitamin B$_1$) | 1.5 mg. |
| Riboflavin (Vitamin B$_2$) | 1.7 mg. |
| Niacinamide | 20.0 mg. |
| Ascorbic Acid (Vitamin C) | 60.0 mg. |
| Pyridoxine (Vitamin B$_6$) | 2.0 mg. |
| Folic Acid | 0.1 mg. |
| Pentothenic Acid | 10.0 mg. |
| Cyanocobalamin (Vitamin B$_{12}$) | 0.5 mg. |
| Cr (acac)$_3$ | 20 μg. |

EXAMPLE V

A Cr (acac)$_3$ fortified peanut butter composition is prepared according to the following formulation:

| Ingredient | Parts by Weight |
|---|---|
| Peanut paste | 90.0 |
| Salt | 1.2 |
| Sucrose | 5.8 |
| Refined sugar | 0.5 |
| Soybean monoglyceride | 0.7 |
| Soybean oil (iodine value 2) | 0.84 |
| Soybean oil (iodine value 107) | 0.40 |
| L threonine (extracted from egg white) | 1.5 |
| N—acetyl-L-methionine | 0.5 |

| Ingredient | Parts by Weight |
|---|---|
| Cr (acac)$_3$ | 0.002 |

EXAMPLE VI

Bleached white flour is fortified with 700 μg of Cr (acac)$_3$ per kg. of flour. The flour is used for baking and any other of its usual purposes without oxidation or degradation of Cr (acac)$_3$.

EXAMPLE VII

Refined sugar is fortified with 400 μg of Cr (acac)$_3$ per kg. of refined sugar. Ingestion of the Cr (acac)$_3$-fortified sugar in the usual daily amounts provides substantial portions of the body's chromium requirements.

EXAMPLE VIII

A unit dose of an insulin-Cr (acac)$_3$ pharmaceutical composition comprises:

| Ingredient | Amount |
|---|---|
| Insulin (commercial solution) | 10 units |
| Cr (acac)$_3$ | 70 μg |

The composition of Example is prepared by mixing the indicated ingredients. Daily intramuscular administration of the composition (hypodermic syringe) to a diabetic patient normalizes blood glucose levels.

Example IX

An oral hypoglycemic agent in unit dosage capsule form comprises:

| Ingredient | Amount |
|---|---|
| Chlorpropamide | 500 mg |
| Cr (acac)$_3$ | 150 μg |

Oral administration of one gelatin capsule per day of the composition of Example X to a patient suffering from diabetes mellitus suffices to normalize blood sugar levels.

EXAMPLE X

In the composition of Example X, the chlorpropamide is replaced by a safe and effective dose of tolbutamide (5 g/day), acetohexamide (15 g/day) and tolazamide (1.5 g/day), respectively, and excellent oral hypoglycemic agents are secured in each instance.

EXAMPLE XI

To a diabetic patient, a Cr (acac)$_3$ capsule of Example I or II is orally administered before or after the intramuscular administration of insulin (commercial solution) to aid in the normalization of the blood glucose level of the patient.

EXAMPLE XII

Timothy hay is fortified with a nutritionally supplemental amount (5 g/2200 kg) of Cr (acac)$_3$ and is suitable for feeding non-ruminant animals.

What is claimed is:

1. A parenterally administerable composition of matter, comprising a mixture of:
   (a) chromium (III) tris-acetylacetonate; and
   (b) insulin, in an amount sufficient to maintain blood glucose at desired levels.

2. A method for treating insulin-dependent diabetes in a patient so afflicted comprising concurrently administering insulin and chromium (III) tris-acetylacetonate to the patient in amounts sufficient to maintain blood glucose at desired levels, the chromium (III) tris-acetylacetonate being administered orally, intramuscularly, intraperitoneally or subcutaneously.

3. A method according to claim 2 wherein the insulin is administered at a rate of from 5 units to about 70 units per day.

* * * * *